United States Patent [19]

Nielsen

[11] Patent Number: 5,288,624
[45] Date of Patent: Feb. 22, 1994

[54] CERCOSPORAL FUNGICIDE COMPOSITIONS AND METHODS OF USE

[75] Inventor: Ruby I. Nielsen, Farum, Denmark

[73] Assignee: Novo Nordisk A/S, Denmark

[21] Appl. No.: 713,463

[22] Filed: Jun. 13, 1991

Related U.S. Application Data

[63] Continuation-in-part of Ser. No. 564,691, Aug. 8, 1990, abandoned, which is a continuation of Ser. No. 271,712, Nov. 16, 1988, abandoned.

[30] Foreign Application Priority Data

Nov. 17, 1987 [DK] Denmark .............................. 6046/87

[51] Int. Cl.$^5$ .................. C12P 1/02; A01N 37/06; A61K 31/22
[52] U.S. Cl. .................................... 435/128; 514/549; 435/171
[58] Field of Search ................. 514/1, 549; 435/252.1, 435/171, 128

[56] References Cited

U.S. PATENT DOCUMENTS

3,928,572 12/1975 Kluepfel et al. ..................... 424/122
4,254,224 3/1981 Onishi et al. ......................... 435/911

FOREIGN PATENT DOCUMENTS

1293227 10/1972 United Kingdom ................ 435/171

OTHER PUBLICATIONS

Endo et al., Mutastein, A New Inhibitor of Adhesive–Insoluble Glucan Synthesis By Glucosyltransferases of Streptococcus Mutans, *The Journal of Antibiotics*, vol. XXXVI, No. 3, pp. 203–207 (Mar. 1983).

Bagli et al., *The Journal of Organic Chemistry* 38(7): 1253–1260 (1973).

*Primary Examiner*—Robert J. Hill, Jr.
*Assistant Examiner*—K. Cochrane Carlson
*Attorney, Agent, or Firm*—Sterne, Kessler, Goldstein & Fox

[57] ABSTRACT

The present invention relates to a funcidally active principle (fungicidal agent) obtainable by cultivation of fungi of the genus Phaeoramularia or Cercospora. The principle can be used for controlling fungi in plants and animals, including mammals.

11 Claims, 1 Drawing Sheet

CERCOSPORAL FUNGICIDE COMPOSITIONS AND METHODS OF USE

CROSS REFERENCE TO RELATED APPLICATION

The present application is a continuation-in-part of application Ser. No. 07/564,691, filed in the United States Patent and Trademark Office on Aug. 8, 1990, now abandoned, which is a continuation of application Ser. No. 07/271,712, filed in the United States Patent and Trademark Office on Nov. 16, 1988, now abandoned.

FIELD OF THE INVENTION

This invention relates to a biochemically active principle (fungicidal agent) obtainable by cultivation of fungi of the genus Phaeoramularia or Cercospora. The invention also relates to fungicidal compositions comprising a fungicidally effective amount of said principle, and agronomically and/or physiologically compatible diluent or a carrier means, and optionally other active materials. The present invention further relates to the fungicidal agent and fungicidal compositions of the present invention for combating fungi in plants or animals, including mammals, and as a preservative in edibles, paints and on timber.

BACKGROUND OF THE INVENTION

Fungi are at present controlled in plants by applying synthetic inorganic or organic fungicides to the area to be treated. Such fungicides are costly and energy consuming in their production, and often they are not very effective in combating the fungi. This may often be due to climatic or environmental conditions prevailing in the area or time of application. Also, the use of a fungicide over a prolonged period of time tends to select for fungi which are tolerant to the fungicide. Most of the known fungicides being alien to the ecosystems wherein they are spread also tend to accumulate and eventually exhibit undesired side effects.

For these and other reasons it is desirable to develop biological fungicides that are easily digested or degraded in nature and do not consume the large amount of energy required for the chemical synthesis of most known fungicides.

The genus Cercospora is known worldwide as the cause of leaf spot diseases on a large number of hosts of different genera. Some species of Cercospora are known to produce different metabolites. For example, *C. betiocola* produces fulvic acid (Sakaki et al., *Agric. Biol. Chem.* 45(5):1275-1276 (1981)) and a yellow phytotoxin (Martin et al., *Proc. Int. Bot. Congr.* 13:296 (1981)).

*C. kikuchii* produces cercosporin (Matsueda, S., Takagaki, K., Shimoyama, M., and Shiota, A. Studies on fungal products. *V. Antimicrobial aspects of Quinone derivatives* and Yakugaku Zasshi 100(9): 900-902 (1980)) and ergosterol-5,8-peroxide (Matsueda, S., Shimoyama, M., Imaizumi, T., Tsushima, Y., *Studies on fungal products* 4. Biological effects of ergosterol-5,8-peroxide. Yakugaku Zasshi 102(4): 347-351 (1982)). Matsueda et al. found cercosporin to inhibit the growth of *Staphylococcus aureus, Bacillus subtilis, Pseudomonas aeruginosa, E. coli* and *Candida japonica*. Cercosporin has been isolated as red crystals, Pfizer Handbook of Microbial Metabolites McGraw-Hill Book Co., Inc. N.Y. Toronto London from Shimpei Kuyama and Teiichi Tamura. *J. Am. Chem. Soc.* 79:5725-5726 (1957).

*C. arachidicola* produces an anthraquinonoid metabolite (Stoessl, A., Stothers, J. B., Minor anthraquinonoid metabolites of Cercospora arachidicola. *Can. J. Chem.* 63(6): 1258-1262 (1985)), and *C. cruenta* produces metabolites structurally related to abscisic acid (Takayuki Oritani, Kyohei Yamashita. Isolation and structure of 4'-hydroxy-γ-ionylidene acetic acids from *Cercospora cruenta,* a fungus producing (+) -Abscisic acid. *Agric. Biol. Chem.* 51(1): 275-278 (1987)), such as mutasteine (Japanese Patent No. 48920 issued 861027). *C. rosicola* produces abscicic acid (Japanese Patent Application No. 192674 filed 8211102).

*C. fusimaculans* has been isolated from a number of grasses (Ellis, M. B., More dematiaceous Hyphomycetes. Commonwealth Mycological Institute, Kew, Surrey, England (1976)) and has been reported to cause foliar disease or sorghum spp. (Wall, G. C., Mughogho, L. K., Frederiksen, R. A., Odvody, G. N. Foliar disease of sorghum spp. caused by *Cercospora fusimaculans. Plant Dis.* 71(8): 759-760 (1987)) and *Bajra Pennisetum* typhoides (Patel, K. S. A. *Cercospora fusimaculans* leaf spot disease of *Bajra Pennisetum* typhoides in *Gujarat. Curr. Sci.* (Bangalore) 42(1): 34). So far there has been no recording of *C. fusimaculans* producing a fungicidally active principle.

SUMMARY OF THE INVENTION

In 1982, *C. fusimaculans* was reclassified and found to be in the genus Phaeoramularia rather than Cercospora. The present invention relates to the unexpected finding that fungi belonging to the genus Phaeoramularia or Cercospora had interesting fungicidal properties. Consequently the present invention relates to a biochemically active principle (fungicidal agent) obtainable by cultivation of fungi of the genus Phaeoramularia, particularly *Phaeoramularia fusimaculans*. The present invention also relates to a fungicidal agent obtainable by cultivating the fungi from the genus Cercospora, particularly *Cercospora setariae*. Such agents have been found to exhibit a unique fungicidal activity.

The invention also relates to a fungicial composition comprising an effective amount of a fungicidally active principle obtainable by cultivation of a fungus of the genus Phaeoramularia or Cercospora and an agrochemically and/or physiologically compatible carrier or diluent.

A further embodiment of the invention relates to a fungicidal composition comprising a suspension of an effective number of spores or mycelium from a fungus of the genus Phaeoramularia or Cercospora in a compatible medium.

Another embodiment of the present invention relates to a method of combating fungi in plants and animals (including mammals), wherein an effective amount of a fungicidally active principle obtainable by cultivation of a fungus of the genus Phaeoramularia or Cercospora is applied to a region to be treated. This aspect of the invention also includes combating or controlling fungi in edibles, timber, paint and the like. The fungicidal agent of the invention may also be used in growth media for microorganisms to prevent fungal contamination in the media.

In yet a fifth embodiment, this invention relates to the use of a fungicidally active principle obtainable by culturing a fungus belonging to the genus Phaeoramularia or Cercospora in controlling fungi in plants or animals, including mammals.

A sixth embodiment of the invention concerns a process for the production of a fungicidally active principle by cultivating a fungus of the genus Phaeoramularia or Cercospora and recovering said active principle.

DEPOSITION OF MICROORGANISMS

Figure 1:
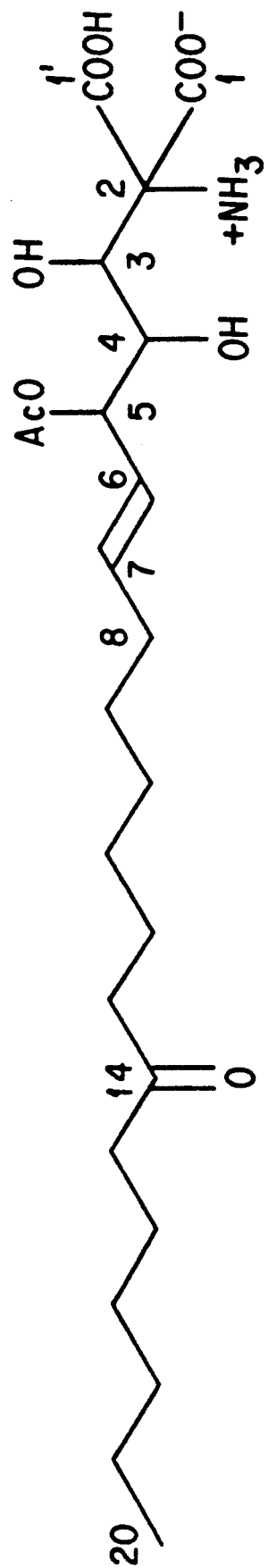
FIG. 1 shows the structure of a fungicidal agent obtained from the genus Phaeoramularia.

A strain used to isolate the fungicidal agent of the present invention is on deposit at the Centraalbureau voor Schimmelcultures (CBS), P.O. Box 273, NL-3740 AB BAARN, Holland for the purposes of patent procedure on the date indicated below. CBS being an international depository authorized under the Budapest Treaty affords permanence of the deposit in accordance with Rule 9, of said Treaty.
Deposit Date: 22 Oct. 1987
Depositors ref: Cercospora fusimaculans Atk
CBS designation: CBS 616.87

It is important to note that the deposited strain has been reclassified as Phaeoramularia fusimaculans (Atk) by Liu and Guo (Studies on Some Species of the Genus Phaeoramularia in China: Acta Phytopathologica Sinica 12:9–10 (1982). The above-noted deposited strain was utilized to isolate the fungicide of the present invention and thus only the name of the fungi has been changed. The deposited strain should hereinafter be designated Phaeoramularia fusimaculans (Atk).

DETAILED DESCRIPTION OF THE INVENTION

The present invention relates to a fungicidally active principle or fungicidal agent obtainable by cultivation of a fungus of the genus Phaeoramularia or Cercospora.

The fungicidal agent of the present invention may also be produced by chemical synthesis techniques well known to those of ordinary skill in the art. Additionally, mutagenesis by common techniques (chemical, ultraviolet light, etc.) may be used to obtain mutant cells capable of producing said fungicidal agent. Thus, one of ordinary skill in the art will recognize that the source of the fungicide of the invention may vary.

The invention also relates to a fungicidal composition comprising an effective amount of a fungicidally active principle obtainable by cultivation of a fungus of the genus Phaeoramularia or Cercospora and an agrochemically and/or physiologically compatible carrier or diluent. Other sources of the fungicidal agent may be used to prepare the fungicidal composition of the present invention.

Depending on the circumstances (such as the type of crop wherein fungi are to be combated, the environmental conditions, or other factors), the fungicidal composition of the present invention in addition to said fungicidally active principle may also contain other active ingredients such as other biocides, pesticides, herbicides, insecticides, nematocides, acaricides or plant nutrients or fertilizers.

For combating fungi in animals, the composition of the invention would usually comprise said active principle alone with a physiologically compatible carrier or diluent, but it may also be combined with other active ingredients such as an antibioticum.

In another embodiment of the invention, a composition comprising a suspension of an effective number of spores or mycelium of a fungus of the genus Phaeoramularia or Cercospora in a compatible medium is provided for. Such a composition is conveniently made by using a liquid growth medium for producing the fungus, which medium subsequently is diluted to a suitable number of viable units (spores and/or mycelium) per ml, typically in the range from $10^2$ to $10^{10}$, and preferably from about $10^4$ to about $10^6$. Subsequently, said suspension is applied to the area to be treated. The amount applied to said area may vary depending on the same circumstances as alluded to above.

In a preferred embodiment of the invention said fungicidally active principle is obtainable by cultivating a fungus of the species Phaeoramularia fusimaculans or Cercospora setariae. In the most preferred embodiment, said species is Phaeoramularia fusimaculans Atk, which on Oct. 22, 1987 was deposited with Centraalbureau voor Schimmelcultures and accorded the accession No. CBS 616.87 or Cercospora setariae, accession number CBS 494.71.

A fungicidal composition according to the invention having the fungicidally active principle as its active ingredient may for agronomical and/or horticultural applications be formulated by mixing the active principle with suitable inert and compatible carriers or diluents to obtain a composition of the type generally used in agricultural composition such as a wetable powder, an emulsifiable concentrate, a granular formulation, a water soluble powder, an alginate, a xanthan gum and/or an aerosol. As solid carriers bentonite, diatomaceous earth, apatite, gypsum, talc, pyrophylite, vermiculite, ground shells, and clay may be used. A surface active agent may also be added with the purpose of producing a homogeneous and stable formulation.

The diluent or carrier in the compositions of the invention can as indicated be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosporic acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkylaryl sulphonates such as alkyl-benzene sulphonates or lower alkylnaphthalene sulphonates, e.g., butyl-napthhalene sulphonate; salts of sulphonated naphthaleneformaldehyde condensates; salts of sulphonated phenol-formaldehyde condensates; or more complex sulphonates such as the amide sulphonates, e.g., the suphonated condensation product of oleic acid and N-methyl taurine or the dialkyl sulphosuccinates, e.g., the sodium sulphonate of dioctyl succinate. Nonionic agents include condensation products of fatty acid esters, fatty alcohols, fatty acid amides or fatty-alkyl- of alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a dispersible powder, an emulsifiable concentrate or granules. Moreover, it can be in a suitable form for direct application or as a concentrate or primary composition which requires dilution with a suitable quantity of water or other diluent before application.

An emulsifiable concentrate comprises the active ingredient dissolved in a water-immiscible solvent which is formed into an emulsion with water in the presence of an emulsifying agent.

A dusting powder comprises the active ingredient intimately mixed and ground with a solid pulverulent diluent, for example, kaolin.

A granular solid comprises the active ingredient associated with similar diluents to those which may be employed in dusting powders, but the mixture is granulated by known methods. Alternatively it comprises the active ingredient absorbed or adsorbed on a pre-granular diluent for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the active ingredient with water or other liquid, a wetting agent and suspending agent.

For use in combating fungi in animals including mammals said active principle may be formulated by mixing said principle with suitable inert and compatible carriers known in the art for use in topical formulations.

The concentration of the active principle described herein in the compositions of the invention may vary within a wide range depending on the type of formulation and the field of application. In connection herewith it is mentioned that tests in the Experimental section have shown the active principle to be efficient to control fungi attacking mammals in concentrations from 0.5 $\mu g/ml$ to 5 $\mu g/ml$ and it is consequently contemplated that the active principle may be applied in concentrations ranging from about 0.01 $\mu g/ml$ to 10 $\mu g/ml$ for use in controlling fungi in animals.

In its third aspect, the invention relates to a method of combating fungi in plants or animals including mammals, wherein an effective amount of a fungicidally active principle obtainable by cultivation of a fungus of the genus Phaeoramularia or Cercospora is applied to a region to be treated.

In connection with this aspect, the compositions of the invention may for agronomical or horticultural uses be applied to a region to be treated either directly to the soil as a pre-emergence treatment or to the foliage or fruits of the plants as a post-emergence treatment. Depending on the crop and circumstances, the treatment may be postponed until seeds or fruits appear on the plants, wherein fungi are to be controlled.

The active preparation or the compositions of the invention can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary.

Sometimes, it is practicable to treat the roots of a plant before or during planting, for example, by dipping the roots in a suitable liquid or solid composition. When the active preparation of the fungicidal agent is applied directly to the plant, a suitable rate of application is from 0.001 to 100 kg per hectare, preferably from 0.05 to 5 kg per hectare.

In the method of the invention, the active preparation of the invention alone or in combination with a conventional biocide can also be applied to seed or habitat. Thus the preparation can be applied directly to the soil before, at or after drilling so that the presence of active ingredient in the soil can control the growth of fungi which may attack seeds.

When the soil is treated directly, the active preparation alone or in admixture with the conventional biocide can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.01 to 20 kg per hectare, more preferably from 0.05 to 10 kg per hectare.

The compositions may be applied in amounts corresponding to from about 1 g to about 100 kg fungicidally active principle per hectare.

For veterinary and medicinal uses, the composition of the invention may be applied to a region to be treated when the diagnosis has been established by the veterinarian or physician.

Although the present invention has been described in detail in connection with controlling fungi in animals and plants, it is also anticipated that the fungicidally active principle may be used for the preservation of wood by adding said principle to wood preservation and/or impregnation compositions. Also, the active principle of the invention may be useful as a fungicide and preservant in paints-both to prevent growth in the paint during storage, and growth on the painted object such as the plastered surface of a house.

Further the fungicially active principle of the invention may, due to its low toxicity, be used for the preservation of edible goods such as jams, marmelade, or other such items where the principle may be added subsequent to any cooking process.

Also the fungicidally active principle of the invention may be used as fungicidal additive to growth media for various microorganisms such as *E. coli, B. subtillis, Pseudomonas aeurgenosa*, and *S. aureus.*

Having now fully described the present invention, the same will be more clearly understood by reference to certain specific examples which are included herewith for purposes of illustration only, and not intended to be limiting of the invention, unless specified.

EXAMPLES

The Fungicidally Active Principle

The fungicidally active principle of the present invention may be produced extracellularly in both surface and submerged substrates containing different carbohydrates and nitrogen sources. When applied in the crude state as it is produced in shake flasks, it has no apparent effect on the growth of *E. coli, Pseudomonas aeruginosa, Bacillus subtilis, Torulopsis ernobii, Rhodotorula ruda, Rhodotorula gracilis, Hansenula holstii, Candida albicans, Penicillium funiculosum, Aspergillus fumigatus, Aspergillus aculeatus, Aspergillus phoenicis, Aspergillus awamori*, and *Staphylococcus aureus*.

The fungicidal active principle of the invention has been found to have an inhibitory effect on the growth of fungi of the following genera Botrytis, Rhizomucor, Pyricularia, Fusarium, Penicillium, and especially on *Botrytis cinerea, Rhizomucor miehei, Pyricularia oryzae, Penicillium digitatum, Cercospora traversiana, Cercospora sorghii, Cercospora sesami, Cercospora scirpicola, Cercospora kikuchii, Cercospora haji, Cercospora beticola, Sclerotinia fructicola, Aspergillus oryzae, Fusarium culmorum, Fusarium decemcellulase, Fusarium acuminatum, Fusarium moniliforme, Fusarium sporotrichioides, Fusarium poae, Fusarium fugikurai, Fusarium longipes, Rhizopus oligosporus*, Trichophyton, Microsporum, Epidermaphyton, Pichia sp., *Torulopsis spherica, Rhodotorula aurantiaca, Rhodotorula glutinis, Rhodotorula minuta, Candida albicans, Trichoderma viride, Drechslera australiensis, Gibberella fugikuri, Phoma herbarum, Pycnoporus sangiuneus, Penicillium rotatum, Penicillium oxalicum, Penicillium crustosum, Penicillium implicatum, Penicillium lividum, Penicillium cyclopium, Penicillium digitatum, Penicillium italicum, Aspergillus cervinus, Aspergillus cremens* and many others.

Matsueda et al. 1980 (supra) found that cercosporin, a compound isolated from *C. kikuchii*, had an inhibitory effect on certain microorganisms. From the preceding paragraph it is obvious that the active principle of the invention is different from cercosporin. Also, a red pigment produced by CBS 616.87, which could contain cercosporin, could readily be separated from the active principle of this invention without affecting the activity of said principle. Said pigment does not exhibit any inhibition on the growth of *Botrytis cinerea*.

The principle of the present invention is active over a wide range of pHs and temperatures but is inactivated when boiled for about one minute. There is no apparent loss of activity when stored as culture broth in the refrigerator for 3 months. In addition, the fungicidal active principle of the present invention shows no indication of mutagenic activity when tested in the presence and absence of the S-9 metabolic activation system (Ames test). Culture broth containing the fungicide and viable spores showed no effect on mice, intraperitoneally applied at the rate of 20 ml per kg body weight. This contained $3 \times 10^8$ viable counts.

The Fungicide Producing Strains

The fungi which produce the active principle of the invention have been identified as belonging to the genus Phaeoramularia. The colonies are mostly hypophyllous. Conidiophores fasciculate, pale olivaceous brown, with small scars. Conidia often catenate, hyaline, nearly always 3-4 septate, $15-70 \times 2-2.5$ μm.

CBS 616.87 was isolated from leaves of *Panicum maximum* collected in St. Andrews, Jamaica in December 1986. It has been identified as *Phaeoramularia fusimaculans*. At the same time, a number of Phaeoramularia producing a fungicidally active principle were isolated from leaves of *P. maximum*, and in August 1988 Phaeoramularia also producing the same similar activity were isolated from leaves of *P. maximum* collected in St. Catherine, Jamaica. The additional isolates of Phaeoramularia capable of producing the active principle were found to be *Phaeoramularia fusimaculaus*. The species can be isolated from leaves of many different grases (Ellis supra).

Further it has been found that *Cercospora setariae* Atkinson deposited with Commonwealth Mycological Institute, Ferry Lane, Kew, Surrey, England, and designated CMI 161118 and CBS 494.71 exhibits production of the fungicidally active principle.

Cultivation of Strains

The fungicide producing strain of the present invention may be grown on agar slants containing the following ingredients in grams/liter: yeast extract 4.0, potassium dihydrogen phosphate 1.0, magnesium sulphate heptahydrate 0.1, glucose 15 and BactoTM (Difco Laboratories, Detroit, USA) agar 20. This substrate is autoclaved at 121° C. for 20 or 40 minutes and will, hereinafter, be referred to as YPG agar. Slants contain 12 ml YPG agar are incubated after inoculation at 20°–25° C. for 7 days or longer.

Fungicide Production

A substrate for shake flasks was prepared with the following ingredients per liter: 4.0 g yeast extract, 1.0 g potassium dihydrogen phosphate, 0.1 g magnesium sulphate heptahydrate, 15 g glucose and 0.1 g Pluronic TM L61 (BASF, Federal Republic of Germany) and demineralized water. Sterilization took place at 121° C. for 20 minutes. A 500 ml Erlenmeyer flask with 100 ml of substrate was inoculated with $10^6$ spores from a YPG agar slant previously inoculated with *Cercospora fusimaculans* CBS 616.87 (now named *Phaeoramularia fusimaculans*). The flasks were shaken at 230 rpm at 25° C. for 3–7 days whereafter the fermentation broth was centrifuged. The supernatant containing the fungicide was thereby separated from the mycelium. The mycelium was discarded and the supernatant was analyzed for fungicidal activity. The fungicide can also be produced in surface cultures.

Analysis

| $10^6$ spores of *Botrytis cinerea* were added to 50 ml of dilute salts | |
|---|---|
| ammonium hydrogen phosphate | 66 mg |
| potassium dihydrogen phosphate | 68 — |
| dipotassium hydrogen phosphate | 87 — |
| calcium chloride-2-hydrate | 7.4 — |
| magnesium chloride-6-hydrate | 10 — |
| made up to 1 liter with distilled water and sterilized at 121° C. for 20 minutes. | |

This was mixed with 50 ml YPG agar at a temperature which favored the viability of Botrytis spores suitably in the termperature range from about 30° C. to about 45° C. where the agar is kept fluid without any harm to the spores. 12 ml of this mixture were poured in 9 cm petri dishes and allowed to solidify. 1–5 holes of 4 mm diameter were punched in the agar and 15 μl culture broth was put in each hole.

The petri dishes were incubated at 20°–25° C. for 2 days. The presence of a fungicide will reveal itself as a clear non-growth zone around the holes—the larger the zone the stronger the fungicide. The supernatant under these conditions produced a clear zone of 25 mm.

Extraction of the Active Principle

The active principle of the invention could be extracted by adsorption on Amberlite XAD-4 adsorbent which has been thoroughly washed with acetone, ethanol and distilled water. Application of the sample on the adsorbent is followed by several washings with distilled water. Elution is carried out with ethanol and acetone, and the active principle concentrated in vacuo at room temperature.

Isolation and Purification of the Active Principle

Culture broth was centrifuged to remove the mycelium. To the centrifugate was added 14 g/l of XAD-8 (Rohm & Haas), and the mixture was stirred at 4° C. for 24 hours. XAD-8 was filtered off and rinsed with 3 volumes of 25% w/w ethanol in 0.1M ammonium acetate (pH 6.0) for 1 hour.

After rinsing, the XAD-8 was extracted twice with 3 volumes of 50% w/w ethanol in 0.1M ammonium acetate (pH 6.0), and twice with 3 volumes of 60% w/w ethanol in 0.1M ammonium acetate (pH 6.0). Each extraction was performed at 5° C. for one hour.

After analysis, the extracts were combined and the density was adjusted to 0.92 g/ml with ethanol prior to addition of 1% active coal (GC Norrit). The suspension obtained was stirred for 2 hours at 5° C., and the coal was removed by filtration. The filtrate was concentrated approximately 40 times by vacuum evaporation at a temperature of maximum 5° C.

At this stage a precipitate formed, which was isolated by centrifugation.

The precipitate was solubilized in 42% v/v ethanol and purified by HPLC by the following procedure.

HPLC PURIFICATION

HPLC system 2 pumps WATERS Model 6000
Hewlett Packard 1040 diode array detector:
Gradient control with MAXIMO ® (Millipore) software
Column: 250×16 mm PLRP-S 20 μm particles.
Eluent:
A: 0.1M ammonium acetate, pH 6.0
B: Acetonitrile, p.a.
Flow: 5 ml/min
Monitor: 230 nm and 280 nm.
Gradient: start: 27% raised to 30% in 70 minutes.
Sample: 2–4 ml
Fraction collector: Gilson Model 201.
Collection start: 30 minutes.

The fractions were analyzed by the bioassay. The active fractions with the highest absorptions at 280 nm compared to 230 nm were concentrated by vacuum evaporation at 5° C. and finally freeze dried.

The freeze dried powder was rechromatographed according to the same procedure and freeze dried.

CHARACTERIZATION OF THE PURIFIED ACTIVE PRINCIPLE

NMR-spectroscopy $^1$H NMR and $^{13}$C NMR spectra for the isolate were established in relation to trimethyl sulfate (TMS) and methanol, respectively, by dissolving the freeze dried powder in methanol-$d_4$ (saturated solution ~2 mg/ml) at a temperature of 297K, and 273K, respectively, and using a Bruker WM 400 instrument at magnetic field strengths of 400 MHz and 100.6 MHz, respectively. For the $^{13}$C-NMR spectrum the number of protons attached to each carbon was determined by INEPT experiment.

The spectra are listed below in Table I.

TABLE I

| $^{13}$C | DEPT | $^1$H/δ (J) |
| --- | --- | --- |
| 214.0 | CO | — |
| 172.5 | CO | — |
| 171.3 | CO | — |
| 170.6 | CO | — |
| 138.8 | CH | 5.86 (H7,dt,7,7,15) |
| 125.7 | CH | 5.45 (H6,dd,8,15) |
| 78.5 | CH | 5.35 (H5,t,8,8) |
| 75.3 | C | — |
| 74.5 | CH | 3.90 (H4,dd,2,8) |
| 70.1 | CH | 4.80 (H3,d,2) |
| 43.5 | CH$_2$ | 2.45 (H13,t,8,8) |
| 43.4 | CH$_2$ | 2.45 (h15,t,8,8) |
| 33.5 | CH$_2$ | 2.06 (H8,m) |
| 32.9 | CH$_2$ | 1.3–1.4 (m) |
| 30.2 | CH$_2$ | 1.3–1.4 (m) |
| 30.1 | CH$_2$ | 1.56 (H12,m) |
| 30.1 | CH$_2$ | 1.54 (H16,m) |
| 29.8 | CH$_2$ | 1.3–1.4 (m) |
| 24.9 | CH$_2$ | 1.3–1.4 (m) |
| 24.6 | CH$_2$ | 1.3–1.4 (m) |
| 23.7 | CH$_2$ | 1.3–1.4 (m) |
| 21.4 | CH$_3$ | 2.05 (Ac,s) |
| 14.5 | CH$_3$ | 0.90 (H20,t,7,7) |

Mass spectroscopy

High resolution mass spectra obtained by positive chemical ionisation using methane, isobutane, and ammonia as ionisation gasses were all in accordance with a molecular formula of $C^{23}H^{39}NO^8$

Structure Elucidation of the Active Principle

The structure of the fungicidal agent has been elucidated as an amino malonic acid derivative. The proposed structure is based on chemical and spectroscopic investigation of the parent compound and an acetate derivative.

The fungicidal agent isolated from a fungus belonging to the genus Phaeoramularia was assigned the structure shown in FIG. 1 based upon chemical and spectroscopic data.

Protection of Grapes Against *Botrytis Cinerea*

Commercially available green grapes were singled off, washed and dried. The pedicels were retained on the fruits. Two holes, 1 mm deep, were made on the fruits with the points of a syringe containing $10^6$/ml of Botrytis spores. The grapes were then incubated at room temperature in a humid atmosphere for 24 hours. They were then inundated in the culture broth and returned to the humid conditions for about 1 week. In another experiment, the fruits were submerged in the culture broth and 24 hours later they were pricked with a syringe containing Botrytis spores. Here, too, they were incubated in a humid atmosphere for about 1 week.

The results of this test are shown in Table II below.

TABLE II

| Type of Treatment | | % Protection | | |
|---|---|---|---|---|
| 1st day | 2nd day | Expt 1 | Expt 2 | *Expt 3 |
| Botrytis cinerea | Water | 0 | 0 | 0 |
| Botrytis cinerea | Culture broth | 66 | 83 | 33 |
| Water | Botrytis cinerea | 0 | 0 | 0 |
| Culture broth | Botrytis cinerea | 66 | 33 | 66 |

*In this experiment a strain of Botrytis cinerea which was resistant to 100 ppm Iprodione (Rhone Poulenc) was used.

As can be seen in Table II, the grapes which were treated with culture broth of CBS 616.87 were very effectively controlled against *Botrytis cinerea* when compared with those treated with water. An even higher degree of protection can be expected if the spores are not injected into the grapes. Also, the protection was obvious when the *Botrytis cinerea* was resistant to known chemical fungicides.

Field Trials for Protection Against *Botrytis Cinerea*

I: Tomato

The fungicide was tested for its ability to protect tomato plants against *Botrytis cinerea* in green houses. Both the controls and the experimentals consisted of 3 plots each of 8 plants measuring 75-90 cm in height. 100 sores were made on the leaves of the 8 plants and they were immediately sprayed to run off with 1% of a freeze-dried sample of the culture broth. The controls were sprayed with water. Four (4) hours later each plant was sprayed with $4 \times 10^6$ spores of *Botrytis cinerea*. The green house was kept at a temperature of 18°-20° C. and a relative humidity of about 90% for 2 weeks after which time the number of infected leaves were counted.

The control plants had a total of 126 infections while those treated with Phaeoramularia fungicide had 44.

II: Peas

20% eluate (see extraction of the active principle) was sprayed on peas (type Bodil) in the field to see if the plants could be protected against natural infection of Botrytis. Four (4) plots each of 30 sq. meters were used for the test and 4 as control. The following compounds were added to the eluate:

0.2% Bevaloid 211, a dispersing agent, (Bevaloid Ltd., P.O. Box 3, Flemingate, Berverley, North Humberside HK 270 NW, England), 1% alcopol, a surfactant (Allied Colloids Ltd., P.O. Box 38, Low Moor, Bradford, Yorkshire BD 120 JZ, England), and 1:1600 of Chevron Spray sticker, ortho product 2786.

The first spraying was done at the onset of flowering and the second 10 days later. When the pods were fully mature and the plants had dried down, 10 plants were chosen at random from each plot and checked in the laboratory for Botrytis infection on the pods and stems. The results below show the average infection per plot.

| TREATMENT | % INFECTION | |
|---|---|---|
| | PODS | STEMS |
| Control | 11 | 63 |
| Phaeoramularia fungicide | 6 | 35 |

Combination with Herbicides

Petri dishes were prepared as described under "Analysis" and used to investigate the effect of herbicides on the Phaeoramularia fungicide. It was found that the fungicide was not affected when combined with Chlorsulfuron (du Pont) (0.05-0.5 mg/ml), Atrazine (Ciba Geigy) (1-10 mg/ml) and Simazine (Ciba Geigy) (0.1-1 mg/ml). Its activity was slightly increased (10-20%) when 0.1-10 mg/ml of Lasso (Monsanto) was added. The 4 herbicides had no effect on Botrytis when applied singly.

The fungicide may be used in cases where *Botrytis cinerea* is resistant to the chemical which are used today. It can be used on fruits and vegetables e.g., grapes, strawberries, tomatoes, citrus fruits and for post harvest protection e.g., on carrots. It may also be used protective or curative on plants which are normally attacked by Botrytis.

Effect of the Fungicide on Dermatophytes

The fungicide produced by CBS 616.87 was tested on *Trichophyton rubrum, T. mentagrophytes* and *Microsporum canis*. These were recent clinical isolates and were cultivated at 25° C. on agar containing the following ingredients in grams per liter:

Bacto Yeast Morphology agar 35, $(NH_4)_2SO_4$ 1.5, $NaH_2PO_4.2H_2O$ 0.429, $K_2HPO_4$ 0.92, 5N NaOH 1 ml.-pH was 7.1. This substrate was sterilized at 121° C. for 20 minutes.

Mycelia from the 3 fungi were disintegrated with sterile glass beads in sterile water and 1 drop applied to the center petri dishes containing the same agar as above but to which was added Phaeoramularia fungicide. The fungicide was added at a concentration of from 0.5 µg/ml to 5 µg/ml of the eluate described under "Extraction of the active principle." Griseofulvin was used in comparison. Controls were prepared with the same agar but devoid of fungicide. Five (5) replicates were made for each test.

All the dishes were incubated at 25° for 5 days after which time they were observed for fungal growth.

The Phaeoramularia fungicide totally prevented the growth of the 3 fungi at all the concentrations tested. That means the MIC was 0.5 µg/ml. The Minimum Inhibitory Concentration, MIC, for griseofulvin is 1.5 µg/ml, 3 µg/ml and 10 µg/ml for *Trichophyton rubrum, Microsporum canis* and *T. mentagrophytes* respectively.

Preservation of Wood

*Poria placenta* and *Gloeophyllum trabeum*, 2 wood inhabiting fungi, were cultivated on malt agar at 25° C. for 4 days. Filter paper discs of 8 mm diameter were wetted with 25 µl eluate containing the fungicidal principle of the invention and placed on the agar at 20 mm from the edge of the actively growing colonies. There were 3 replicates. Further incubation showed that growth of the 2 fungi was strongly inhibited by the fungicide.

Modifications of the above-described modes for carrying out the invention that are obvious to persons of skill in microbiology, agricultural chemistry, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A substantially pure fungicidal agent comprising the structure:

$$\underset{20}{\sim}\underset{14}{\sim}\underset{\underset{O}{\parallel}}{\sim}\underset{7}{\sim}\underset{5}{\sim}\underset{OH}{\overset{AcO}{\underset{3}{\vert}}}\underset{OH}{\overset{OH}{\underset{+NH_3}{\vert}}}\underset{COO^-}{\overset{1'}{\underset{COOH}{}}}$$

2. A fungicidal composition comprising an effective amount of the fungicidal agent of claim 1 in an agrochemically compatible carrier or diluent.

3. The fungicidal composition of claim 2 further comprising herbicides.

4. A fungicidal composition comprising an effective amount of the fungicidal agent of claim 1 in a physiologically compatible carrier or diluent.

5. A method of combatting fungi in plants, wherein an effective amount of the fungicidal agent of claim 1 is applied to a plant region afflicted with said fungi.

6. The method of claim 5, wherein said fungi is from the genus Botrytis.

7. The method of claim 6, wherein said fungi is *Botrytis cinerea*.

8. A method of combatting fungi in mammals, wherein an effective amount of the fungicidal agent of claim 1 is applied to a region of the animal afflicted with said fungi.

9. The method of either claim 5 or 8, wherein said fungi is selected from the group consisting of: *Botrytis cinerea, Rhizomucor miehei, Pyricularia oryzae, Penicillium digitatum, Cercospora traversiana, Cercospora sorghii, Cercospora sesami, Cercospora scirpicola, Cercospora kikuchii, Cercospora haji, Cercospora beticola, Sclerotinia fructicola, Aspergillus oryzae, Fusarium culmorum, Fusarium decemcellulase, Fusarium acuminatum, Fusarium moniliforme, Fusarium sporotrichioides, Fusarium poae, Fusarium fugikurai, Fusarium longipes, Rhizopus oligosporus*, Trichophyton, Microsporum, Epidermaphyton, Pichia sp., *Torulopsis spherica, Rhodotorula aurantiaca, Rhodotorula glutinis, Rhodotorula minuta, Candida albicans, Trichoderma viride, Drechslera australiensis, Gibberella fugikuri, Phoma herbarum, Pycnoporus sangiuneus, Penicillium rotatum, Penicillium oxalicum, Penicillium crustosum, Penicillium implicatum, Penicillium lividum, Penicillium cyclopium, Penicillium digitatum, Penicillium italicum, Aspergillus cervinus* or *Aspergillus cremens*.

10. A process for the production of the fungicidal agent of claim 1, wherein *Phaeoramularia fusimaculans* (Atk accession no. CBS 616.87) or *Cercospora setariae* (accession no. CBS 494.71) is cultivated in the presence of sources of assimilable nitrogen, carbon, oxygen, and essential nutrients and the fungicidal agent is recovered.

11. The process of claim 10, wherein said *Phaeoramularia fusimaculans* (Atk accession number CBS 616.87) or *Cercospora setariae* (accession number CBS 494.71) is mutated to produce daughter cells with increased production of said fungicidal agent.

* * * * *

UNITED STATES PATENT AND TRADEMARK OFFICE
CERTIFICATE OF CORRECTION

PATENT NO. : 5,288,624
DATED : February 22, 1994
INVENTOR(S) : Ruby lone Nielsen It is certified that error appears in the above-indentified patent and that said Letters Patent is hereby corrected as shown below:

Column 10, line 44, delete "$C^{23}H^{39}NO^{8}$" and replace therein -- $C_{24}H_{37}NO_{6}$ --.

Signed and Sealed this

Twentieth Day of September, 1994

Attest:

BRUCE LEHMAN

Attesting Officer    Commissioner of Patents and Trademarks